United States Patent [19]

Lok et al.

[11] Patent Number: 5,700,631

[45] Date of Patent: Dec. 23, 1997

[54] PHOTOGRAPHIC ELEMENT CONTAINING NEW GOLD(I) COMPOUNDS

[75] Inventors: Roger Lok, Rochester; Weimar Weatherly White, Canaseraga, both of N.Y.

[73] Assignee: Eastman Kodak Company, Rochester, N.Y.

[21] Appl. No.: 672,254

[22] Filed: Jun. 28, 1996

Related U.S. Application Data

[63] Provisional application No. 60/002,696, Jul. 31, 1995 and a continuation-in-part of Ser. No. 616,016, Mar. 14, 1996, abandoned.

[51] Int. Cl.$^6$ .................... G03C 1/09; C07F 1/12
[52] U.S. Cl. ................... 430/605; 430/567; 430/569; 430/603
[58] Field of Search ................... 430/603, 605, 430/567, 569; 556/113

[56] References Cited

U.S. PATENT DOCUMENTS

| | | | |
|---|---|---|---|
| 3,503,749 | 3/1970 | Tavenier et al. | |
| 4,165,380 | 8/1979 | Hill | 424/290 |
| 4,198,240 | 4/1980 | Mikawa | 430/570 |
| 4,276,374 | 6/1981 | Mifune et al. | 430/611 |
| 4,960,689 | 10/1990 | Nishikawa et al. | 430/603 |
| 5,001,042 | 3/1991 | Hasebe | 430/382 |
| 5,009,992 | 4/1991 | Friedrich et al. | 430/573 |
| 5,017,468 | 5/1991 | Joly et al. | 430/569 |
| 5,043,256 | 8/1991 | Otani | 430/550 |
| 5,043,259 | 8/1991 | Arai | 430/596 |
| 5,049,485 | 9/1991 | Deaton | 430/605 |
| 5,081,009 | 1/1992 | Tanemura et al. | 430/569 |
| 5,104,784 | 4/1992 | Shuto et al. | 430/567 |
| 5,110,719 | 5/1992 | Shuto et al. | 430/569 |
| 5,185,241 | 2/1993 | Inoue | 430/598 |
| 5,229,263 | 7/1993 | Yoshida et al. | 430/600 |
| 5,252,455 | 10/1993 | Deaton | 430/605 |
| 5,266,442 | 11/1993 | Ooms | 430/265 |
| 5,283,169 | 2/1994 | Goto | 430/603 |
| 5,292,635 | 3/1994 | Lok | 430/611 |
| 5,484,690 | 1/1996 | Goto | 430/435 |

FOREIGN PATENT DOCUMENTS

| | | | |
|---|---|---|---|
| 0 457 298 A1 | 5/1991 | European Pat. Off. | G03C 1/08 |
| 0 514 675 A1 | 11/1992 | European Pat. Off. | G03C 1/09 |
| 2/189541-A | 1/1989 | Japan | G03C 1/28 |
| 3/100-542-A | 9/1989 | Japan | G03C 1/06 |
| 05/313282-A | 4/1991 | Japan | G03C 1/08 |
| 05/053234-A | 8/1991 | Japan | G03C 1/09 |
| 06/242536-A | 12/1992 | Japan | G03C 1/07 |

OTHER PUBLICATIONS

"Gold(1) Complexes of Unidentate and Bidentate Phosphorus–, Arsenic–, Antimony–, and Sulphur–donor Ligands" by C. McAuliffe, et al., 1979, pp. 1730–1735 J. C. S. Dalton.
"Photographic Printing in Colloidal Gold" by M.J. Ware, pp. 157–161 J. of Photo. Sci. vol. 42, 1994.

*Primary Examiner*—Mark F. Huff
*Attorney, Agent, or Firm*—Peter C. Cody; Sarah Meeks Roberts

[57] ABSTRACT

A photographic element is provided comprising a support having situated thereon a silver halide emulsion layer, the emulsion layer comprising a compound of the formula:

$$Z-SO_2S-Au(I)-L \qquad (I)$$

wherein

Z represents an alkyl, aryl, or heterocyclic group; and
L represents a thioether, selenoether or telluroether containing ligand.

20 Claims, No Drawings

PHOTOGRAPHIC ELEMENT CONTAINING NEW GOLD(I) COMPOUNDS

CROSS-REFERENCE TO RELATED APPLICATIONS

This is a continuation-in-part application of U.S. Ser. No. 08/616,016, filed Mar. 14, 1996, entitled "PHOTOGRAPHIC ELEMENT CONTAINING NEW GOLD(I) COMPOUNDS", now abandoned, which claims the benefit of U.S. Provisional Application No. 60/001,696, filed Jul. 31, 1995.

FIELD OF THE INVENTION

This invention relates to new gold(I) compounds comprising a thiosulfonate containing ligand, and to photographic elements containing such compounds.

BACKGROUND OF THE INVENTION

For more than a century, it has been known that certain materials are sensitive to actinic radiation and, upon exposure to such radiation, form latent images capable of being subsequently developed into useful visible images. Almost exclusively, commercial application of these radiation sensitive materials has been the domain of silver halides which exhibit superior sensitivity to light over other radiation sensitive materials, some of which have been known for as long as silver halides have been in use. Such superior sensitivity has made silver halides more practical for use in cameras and other photographic equipment since they can be utilized in low light situations, or in situations where the mechanical characteristics of a camera (or other exposure means) would interfere with an optimum exposure.

Despite their superior sensitivity to light, there nevertheless has been considerable effort devoted to improving the sensitivity of silver halide crystals, and hence the photographic elements in which they are contained. In this regard, photographic chemists have attempted to vary the processes for making, or the components within, silver halide emulsions. One particularly preferred means by which to improve sensitivity has been to chemically sensitize photographic emulsions with one or more compounds containing labile atoms of gold, sulfur, selenium or the like. Examples of chemically sensitized photographic silver halide emulsion layers are described in, for example, *Research Disclosure*, Item No. 308119, Dec. 1989, Section III, and the references listed therein. (*Research Disclosure* is published by Kenneth Mason Publications Ltd, Dudley Annex, 12a North Street, Emsworth, Hampshire PO 10 7DQ, England.)

Among the gold(I) chemical sensitizers known in the industry, trisodium aurous dithiosulfate is often cited as being advantageous. This compound, however, is not universally applicable to all emulsion systems because of certain disadvantages it provides. In particular, trisodium aurous dithiosulfate contains two thiosulfate ions that are bonded to gold. These ions may undergo sulfur sensitization reactions in addition to the gold sensitization reactions in the emulsion. Therefore, this gold(I) compound is not appropriate in silver halide compositions in which a ratio of sulfur to gold of less than 2:1 is desired for chemical sensitization, and not appropriate in silver halide compositions in which sulfur or selenium sensitizers other than thiosulfate are desired.

Other known gold(I) chemical sensitizers include aurous sulfides and the gold(I) thiolate compounds as described in Tavenier et al., U.S. Pat. No. 3,503,749. With respect to the former, although relatively easy to manufacture, they have been known to provide considerable sensitization variability and thus more predictable alternatives are desired. With respect to the latter compounds, they contain a sulfonic acid substituent on the thiolate ligand to impart water solubility. Further, they require the use of gold fulminate in their manufacture, a compound that is dangerously explosive and thus not desirable for practical use.

In Deaton, U.S. Pat. No. 5,049,485, a new class of gold(I) compounds comprising mesoionic ligands is described. Specifically, gold(I) compounds are described which contain one or two mesoionic substituents bound directly to a gold atom. The compounds are also positively charged, and thus must be associated with an appropriate anion, typically a halogen or tetrafluoroborate.

The compounds described in U.S. Pat. No. 5,049,485 are advantageous in that they provide gold(I) sensitization without many of the disadvantages inherent in the use of the aforementioned gold(I) compounds. However, they have been known to exhibit limited stability in solution or dispersion. Further, they offer only limited sensitivity improvement, and at certain levels and under certain photographic conditions, they can cause an undesirable increase in fog.

It would thus be desirable to identify alternative gold(I) compounds that can provide a high degree of chemical sensitization without a concurrent and substantial rise in fog levels. These compounds should be stable in solution or dispersion and should be suitable for multiple types of emulsion systems. Further, they should be readily synthesizable in the absence of dangerous reactants.

SUMMARY OF THE INVENTION

The present invention provides new gold(I) compounds of the formula below, and photographic elements that comprise a support having situated thereon a silver halide emulsion layer, the emulsion layer comprising a compound of the formula:

$$Z-SO_2S-Au(I)-L \qquad (I)$$

wherein

Z represents an alkyl, aryl, or heterocyclic group; and

L represents a thioether, selenoether or telluroether containing ligand.

The invention also provides a method of forming a silver halide emulsion comprising precipitating silver halide grains in an aqueous colloidal medium, washing the grains, and sensitizing the grains by adding dyes, chemical sensitizers, and heating, and adding to the emulsion, prior to or during heating, a compound of the above formula.

The invention provides the opportunity to achieve improved chemical sensitization in various types of silver halide photographic elements by use of a new type of gold(I) compound. The gold(I) compound also offers improved stability over prior known gold(I) compounds. It further provides the opportunity to achieve chemical sensitization without a concurrent and substantial rise in fog.

DETAILED DESCRIPTION OF THE INVENTION

In accordance with the invention, a photographic element is provided which comprises a gold(I) compound of the formula:

$$Z-SO_2S-Au\,(I)-L \qquad (I)$$

wherein

Z represents an alkyl, aryl, or heterocyclic group; and

L represents a thioether, selenoether or telluroether containing ligand.

By alkyl, aryl, or heterocyclic group, in either the description of Z or elsewhere in this application, it is meant such groups as defined in accordance with the definitions set forth in Grant and Hackh's *Chemical Dictionary*, fifth ed., McGraw-Hill 1987, and in accordance with general rules of chemical nomenclature.

Exemplary alkyl groups include methyl, ethyl, propyl, butyl, pentyl, hexyl, octyl, nonyl, decyl, dodecyl, hexadecyl, octadecyl, isopropyl, and t-butyl. Preferably, the alkyl groups have from 1 to 5 carbon atoms, although groups having as many as 20 carbon atoms or more are specifically contemplated.

Exemplary aryl groups include phenyl, tolyl, naphthyl, biphenyl, azulenyl, anilinyl, and anisidinyl. It is preferred that such groups have from 6 to 20 carbon atoms. More preferred are groups selected from phenyl, tolyl, and naphthyl.

Exemplary heterocyclic groups (which include heteroaryl groups) include pyrrolyl, furanyl, tetrahydrofuranyl, pyridinyl, picolinyl, piperidinyl, morpholinyl, thiadiazolyl, thiatriazolyl, benzothiazolyl, benzoxazolyl, benzimidizolyl, benzoselenozolyl, benzotriazolyl, indazolyl, quinolinyl, quinaldinyl, pyrrolidinyl, thiophenyl, oxazolyl, thiazolyl, imidazolyl, selenazolyl, tellurazolyl, triazolyl, tetrazolyl, and oxadiazolyl. It is preferred that the heterocyclic group be selected from triazolyl, tetrazolyl and thiazolyl.

Each of the above groups may be substituted with other groups, such groups being readily determinable by those skilled in the art for providing the advantages of the invention. Groups suitable for substitution on each include alkyl and alkylene groups (for example, methyl, ethyl, ethylene, hexyl, hexylene), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups (or salts thereof), cyano groups, sulfo groups (or salts thereof), and amino groups.

The ligand in formula (I), as described above, is a thioether, selenoether or telluroether, preferably one in which the sulfur, selenium or tellurium atom is complexed directly to the gold(I) atom. Preferably, the thioether, selenoether or telluroether ligand has a molecular weight of from about 60 to about 2000; and optimally from about 100 to about 500.

The thioether, selenoether or telluroether ligand preferably has directly attached to the chalcogen atom at least one aliphatic carbon group. By aliphatic, it is meant acyclic. Thus, at least one of the groups to which the sulfur, selenium or tellurium atom is attached originates with a carbon atom that does not form part of a ring or ring system. The carbon atom, however, can be substituted with additional substituents, some of which may be, or may contain, ring or ring systems such as the aryl or heterocyclic groups described above.

The ligand represented by L in formula (I) is preferably of the formula:

$$(R^7)_p-\underset{R^6}{\overset{R^5}{C}}-\left(\underset{R^2}{\overset{R^1}{C}}\right)_m-X^*-\left(\underset{R^4}{\overset{R^3}{C}}\right)_n-\underset{R^9}{\overset{R^8}{C}}-R^{10} \quad (II)$$

wherein

X is a sulfur or selenium atom;

* denotes the point of attachment (i.e. complexation) of L to Au(I);

$R^1$ to $R^4$ are independently hydrogen or an alkyl, aryl or heteroaryl group;

$R^5$ and $R^6$ are bonded together to form an aryl or heteroaryl group, or are independently hydrogen, carboxy, sulfo, amino, or an alkyl, aryl or heteroaryl group;

$R^7$, $R^8$, $R^9$ and $R^{10}$ are independently hydrogen, carboxy, sulfo, amino or an alkyl, aryl or heteroaryl group;

n and m are independently 0 to 20; and p is 0 or 1, with the proviso that if $R^5$ and $R^6$ are bonded together to form an aryl or heteroaryl ring, p is 0; and if $R^5$ and $R^6$ are not so bonded, p is 1.

More preferably, L is represented by the formula:

$$R^7-\underset{R^6}{\overset{R^5}{C}}-(H_2C)_m X^*(CH_2)_n-\underset{R^9}{\overset{R^8}{C}}-R^{10} \quad (III)$$

wherein

X is a sulfur atom;

* denotes the point of attachment (i.e. complexation) of L to Au(I);

$R^5$ and $R^8$ are independently hydrogen or an alkyl group having from 1 to 10 carbon atoms or an aryl group having from 5 to 10 carbon atoms;

$R^6$, $R^7$, $R^9$ and $R^{10}$ are independently hydrogen, carboxy, amino or an alkyl group having from 1 to 6 carbon atoms; and n and m are independently 0 to 10.

In the most preferred embodiments of the invention, the gold(I) compound is selected from the following group. These compounds are representative examples of the gold(I) compounds utilized in the invention and should not to be construed as limiting the invention thereto.

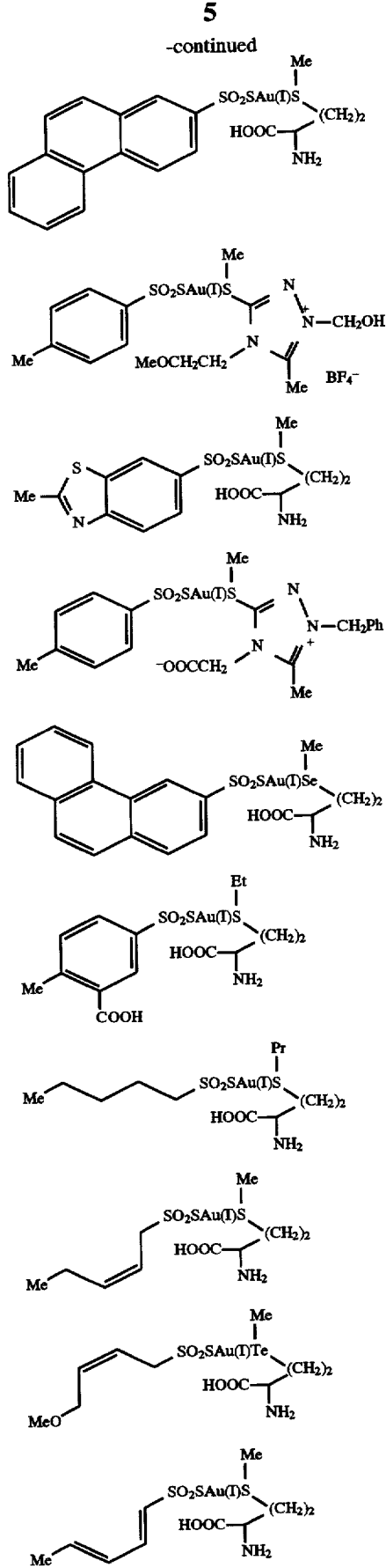
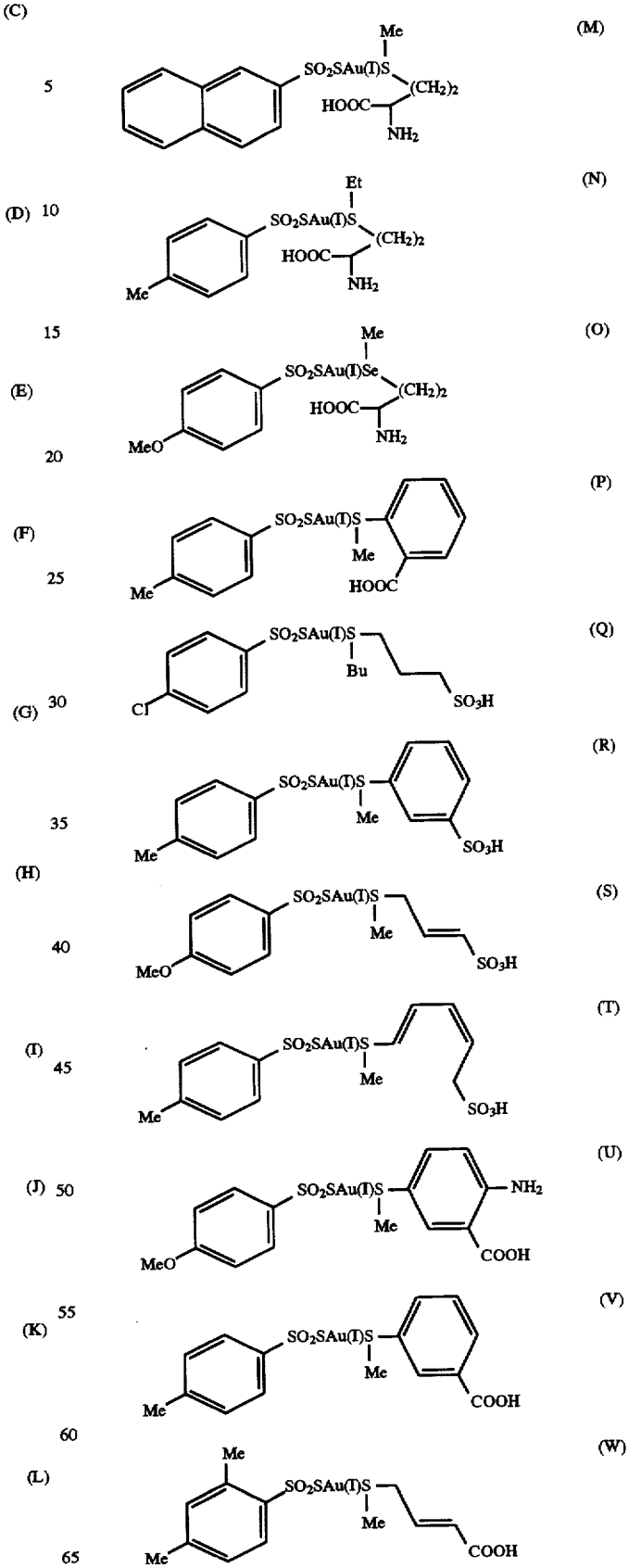

-continued

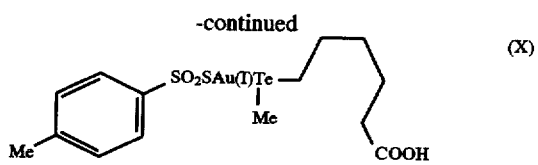

(X)

In the practice of the present invention, the silver halide emulsion layer comprising the gold(I) compound may be comprised of any halide distribution. Thus, it may be comprised of silver chloride, silver bromide, silver bromochloride, silver chlorobromide, silver iodochloride, silver iodobromide, silver bromoiodochloride, silver chloroiodobromide, silver iodobromochloride, and silver iodochlorobromide emulsions. It is preferred, however, that the emulsion be a predominantly silver chloride emulsion. By predominantly silver chloride, it is meant that the grains of the emulsion are greater than about 50 mole percent silver chloride. Preferably, they are greater than about 75 mole percent silver chloride; more preferably greater than about 90 mole percent silver chloride; and optimally greater than about 95 mole percent silver chloride.

The silver halide emulsion employed in the practice of the invention can contain grains of any size and morphology. Thus, the grains may take the form of cubes, octahedrons, cubo-octahedrons, or any of the other naturally occurring morphologies of cubic lattice type silver halide grains. Further, the grains may be irregular such as spherical grains or tabular grains. Particularly preferred are grains having a tabular or cubic morphology.

The photographic emulsions employed in this invention are generally prepared by precipitating silver halide crystals in an aqueous colloidal medium (matrix) by methods known in the art. The colloid is typically a hydrophilic film forming agent such as gelatin, alginic acidt or derivatives thereof.

The crystals formed in the precipitation step are washed and then chemically and spectrally sensitized by adding spectral sensitizing dyes and chemical sensitizers, and by providing a heating step during which the emulsion temperature is raised, typically from 40° C. to 70° C. and maintained for a period of time. The precipitation and spectral and chemical sensitization methods utilized in preparing the emulsions employed in the invention can be those methods known in the art.

Chemical sensitization of the emulsion typically employs sensitizers such as: reducing agents, e.g., polyamines and stannous salts; noble metal compounds, e.g., gold, platinum; and polymeric agents, e.g., polyalkylene oxides. As described, heat treatment is employed to complete chemical sensitization. Spectral sensitization is effected with a combination of dyes, which are designed for the wavelength range of interest within the visible or infrared spectrum. It is known to add such dyes both before and after heat treatment.

After sensitization, the emulsion is coated on a support. Coating techniques known in the art include dip coating, air knife coating, curtain coating and extrusion coating.

The gold(I) compounds can be added to the emulsion at any time, such as during the grain growth, during or before chemical sensitization or during final melting and co-mixing of the emulsion and additives for coating. It is preferred that the compounds be added after precipitation of the grains, and most preferred that they be added before or during the heat treatment of the chemical sensitization step.

The gold(I) compounds can be introduced to the emulsion at the appropriate time by any means commonly practiced in the art such as by a gel dispersion. In one particularly preferred embodiment of the invention, an emulsion is prepared by precipitating silver halide grains in a first aqueous colloidal medium, washing the grains, sensitizing the grains by adding dyes, chemical sensitizers and heating, and adding to the emulsion, prior to or during heating, a dispersion prepared by combining a thiosulfonate compound with potassium tetrachloraurate and a thioether, selenoether or telluroether compound in a second aqueous colloidal medium. It is believed that the compounds react in the second aqueous colloidal medium to form the gold (I) compounds of the invention.

The thiosulfonate compound is typically the salt (e.g., sodium salt) of an arylthiosulfonate such as tolythiosulfonate; but it can be any of the thiosulfonate compounds known in the art and utilized in the photographic industry, for example, those described in U.S. Pat. Nos. 4,960,689 and 5,110,719 and U.S. Statutory Invention Registration H706, all of which are incorporated herein by reference. Preferably, the thiosulfonate compound is utilized in combination with a sulfinate compound such as tolylsulfinate.

Preferably, the ether utilized is a thioether or selenoether; and more preferably, it is a thioether such as methionine. Other dialkyl or alkyl aryl thioethers are also preferred. Most preferably, the thioether contains a water solubilizing group such as a carboxy or sulfo group(or salts thereof); and optimally, it contains a water solubilizing group and an amino group.

The silver halide grains, aqueous colloidal media, dyes, and washing and chemical sensitization steps, can be any of those described previously or subsequently and are exemplified in the art.

The gold(I) compounds may also be added to the vessel containing the aqueous gelatin salt solution before the start of the precipitation; or to a salt solution during precipitation. Other modes are also contemplated. Temperature, stirring, addition rates and other precipitation factors may be set within conventional ranges, by means known in the art, so as to obtain the desired physical characteristics.

A suitable level for the gold(I) compounds is from about 0.0001 to about 1 millimole/mole silver, depending upon the particular properties of the silver halide emulsion in which it is incorporated. A preferred level is from about 0.001 to about 0.1 millimole/mole silver. A more preferred level is from about 0.01 to about 0.1 millimole/mole silver; and an optimal level is about 0.05 millimole/mole silver.

In the following Table, reference will be made to (1) Research Disclosure, December 1978, Item 17643, (2) Research Disclosure, December 1989, Item 308119, and (3) Research Disclosure, September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein.

| Reference | Section | Subject Matter |
| --- | --- | --- |
| 1 | I, II | Grain composition, morphology and preparation. Emulsion preparation including hardeners, coating aids, addenda, etc. |
| 2 | I, II, IX, X, XI, XII, XIV, XV | |
| 3 | I, II, III, IX A & B | |
| 1 | III, IV | Chemical sensitization and spectral sensitization/ desensitization |
| 2 | III, IV | |
| 3 | IV, V | |
| 1 | V | UV dyes, optical brighteners, luminescent dyes |
| 2 | V | |
| 3 | VI | |
| 1 | VI | Antifoggants and stabilizers |
| 2 | VI | |
| 3 | VII | |

-continued

| Reference | Section | Subject Matter |
|---|---|---|
| 1 | VIII | Absorbing and scattering materials; Antistatic layers; matting agents |
| 2 | VIII, XIII, XVI | |
| 3 | VIII, IX C & D | |
| 1 | VII | Image-couplers and image-modifying couplers; Dye stabilizers and hue modifiers |
| 2 | VII | |
| 3 | X | |
| 1 | XVII | Supports |
| 2 | XVII | |
| 3 | XV | |
| 3 | XI | Specific layer arrangements |
| 3 | XII, XIII | Negative working emulsions; Direct positive emulsions |
| 2 | XVIII | Exposure |
| 3 | XVI | |
| 1 | XIX, XX | Chemical processing; Developing agents |
| 2 | XIX, XX, XXII | |
| 3 | XVIII, XIX, XX | |
| 3 | XIV | Scanning and digital processing procedures |

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposedby x-rays, they can include features found in conventional radiographic elements.

The photographic elements are preferably exposed to actinic radiation, typically in the visible region of the spectrum, to form a latent image, and then processed to form a visible image, preferably by other than heat treatment. Processing is preferably carried out in the known RA-4™ (Eastman Kodak Company) developing solutions.

SYNTHETIC EXAMPLE

The following example illustrates the synthesis of a gold(I) compound useful in the present invention. The synthesis described is representative and can be readily varied by those skilled in the art to obtain other useful gold(I) compounds.

To 40.0 ml of water, 7.7074 g of potassium tetrachloroaurate were added and dissolved to form Solution A. A second solution, Solution B, was prepared by dissolving 15.168 g of methionine in 315.0 g of water. Solution A was added to Solution B and the mixture was stirred and filtered. The filtrate was added to a solution of 3.32 g of gelatin (12.5% water) in 100 g of water to form Solution C. Solution C was heated to 40° C. and then cooled to room temperature. An aqueous solution of tolylthiosulfonate and tolylsulfinate prepared by adding 4.766 g of tolylthiosulfonate potassium salt and 0.48 g of tolylsulfinate sodium salt to 235.72 g of water was then added to Solution C to form a gold(I) compound, specifically Compound A.

EXAMPLES

The practice of the invention is described in detail below with reference to specific illustrative examples, but the invention is not to be construed as being limited thereto.

Example 1

Various amounts of a dispersion of the gold(I) compound prepared above or a comparative compound (as shown in Table I) were added alone or in a gelatin dispersion to a series of 0.3 mole tabular [100]grain negative silver chloride emulsions at 40° C. A blue spectral sensitizing dye, anhydro-5-chloro-3,3'-di(3-sulfopropyl) naphtho[1,2-d] thiazolothiacyanine hydroxide triethylammonium salt (550 mg/Ag mol) was added to the emulsions which were stirred for 20 minutes. The emulsions were heated to 60° C., held for 40 minutes, and then cooled to 40° C. A solution of 1-(3-acetamidophenyl)-5-mercaptotetrazole (100 mg/Ag mol) was added and the emulsions chilled and readied for coating. The emulsions further contained a yellow dye-forming coupler alpha-(4-(4-benzyloxy-phenyl-sulfonyl) phenoxy)-alpha(pivalyl)-2-chloro-5-(gamma-(2,4-di-5-amylphenoxy)butyramido)acetanilide (1.08 g/m$^2$) in di-n-butylphthalate coupler solvent (0.27 g/m$^2$), and gelatin (1.51 g/m$^2$). The emulsions (0.34 g Ag/m$^2$) were coated on a resin coated paper support and a 1.076 g/m$^2$ gel overcoat was applied as a protective layer along with the hardener bis (vinylsulfonyl) methyl ether in an amount of 1.8% of the total gelatin weight. The coatings were given a 0.1 second exposure, using a 0–3 step tablet (0.15 increments) with a tungsten lamp designed to stimulate a color negative print exposure source. This lamp had a color temperature of 3000 K, log lux 2.95, and the coatings were exposed through a combination of magenta and yellow filters, a 0.3 ND (Neutral Density), and a UV filter. The processing consisted of a color development (45 sec, 35° C.), bleach-fix (45 sec, 35° C.) and stabilization or water wash (90 sec, 35° C.) followed by drying (60 sec, 60° C.). The chemistry used in the processor consisted of the following solutions:

| Developer: | |
|---|---|
| Lithium salt of sulfonated polystyrene | 0.25 mL |
| Triethanolamine | 11.0 mL |
| N,N-diethylhydroxylamine (85% by wt.) | 6.0 mL |
| Potassium sulfite (45% by wt.) | 0.5 mL |
| Color developing agent (4-(N-ethyl-N-2-methanesulfonyl aminoethyl)-2-methyl-phenylenediaminesesquisulfate monohydrate | 5.0 g |
| Stilbene compound stain reducing agent | 2.3 g |
| Lithium sulfate | 2.7 g |
| Acetic acid | 9.0 mL |
| Water to total 1 liter, pH adjusted to 6.2 | |
| Potassium chloride | 2.3 g |
| Potassium bromide | 0.025 g |
| Sequestering agent | 0.8 mL |
| Potassium carbonate | 25.0 g |
| Water to total of 1 liter, pH adjusted to 10.12 | |

| Bleach-fix | |
|---|---|
| Ammonium sulfite | 58.0 g |
| Sodium thiosulfate | 8.7 g |
| Ethylenediaminetetracetic acid ferric ammonium salt | 40.0 g |

| Stabilizer | |
|---|---|
| Sodium citrate | 1.0 g |
| Water to total 1 liter, pH adjusted to 7.2 | |

Speed and fog data were determined for each of the fresh coatings and are shown below in Table I. Speed was measured at 1.0 density units above Dmin and represents emulsion sensitivity. Fog was measured as the minimum density (Dmin) above zero. All amounts of the gold(I) and comparative compounds are shown in μmol/Ag mol. The structures of comparative compounds utilized in the Examples of Table I are shown following Table I.

TABLE I

| Sample | Compound | Amount | Speed | Fog |
|---|---|---|---|---|
| 1 (control) | none | 0 | 112 | 0.072 |
| 2 (invention) | A | 0.235 | 121 | 0.083 |
| 3 (invention) | A | 0.470 | 126 | 0.086 |
| 4 (invention) | A | 1.175 | 143 | 0.126 |
| 5 (invention) | A | 1.763 | 153 | 0.100 |
| 6 (invention) | A | 2.35 | 162 | 0.114 |
| 7 (invention) | A | 2.938 | 166 | 0.099 |
| 8 (comparison) | C-1 | 0.235 | 113 | 0.077 |
| 9 (comparison) | C-1 | 1.175 | 111 | 0.074 |
| 10 (comparison) | C-1 | 1.763 | 109 | 0.079 |
| 11 (comparison) | C-1 | 2.35 | 112 | 0.067 |
| 12 (comparison) | C-1 | 2.938 | 108 | 0.075 |
| 13 (comparison) | C-2 | 0.235 | 109 | 0.071 |
| 14 (comparison) | C-2 | 1.175 | 111 | 0.078 |
| 15 (comparison) | C-2 | 1.763 | 111 | 0.073 |
| 16 (comparison) | C-2 | 2.35 | 112 | 0.099 |
| 17 (comparison) | C-2 | 2.938 | 107 | 0.073 |
| 18 (comparison) | C-3 | 0.235 | 121 | 0.090 |
| 19 (comparison) | C-3 | 1.175 | 122 | 0.165 |
| 20 (comparison) | C-3 | 1.763 | 130 | 0.221 |
| 21 (comparison) | C-3 | 2.35 | 133 | 0.313 |
| 22 (comparison) | C-3 | 2.938 | 135 | 0.323 |

Comparative compounds utilized in the examples and not previously described are as follows:

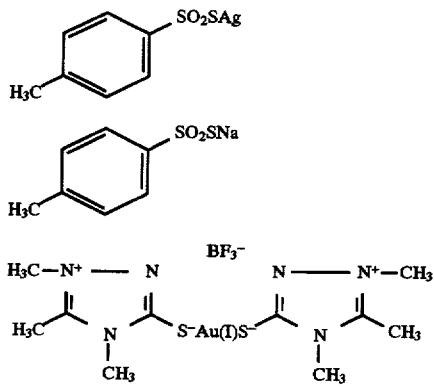

It can be seen in Table I that the samples of the present invention (2–7) provide the most improved sensitivity, and do so with only a minimal rise in fog levels.

Example 2

Various amounts of the gold(I) compound prepared above or a comparative compound (as shown in Table II) were added to a series of 0.3 mole cubic chloride emulsions (edge length 0.78 μm) at 40° C. The emulsions were heated to 60° C. and held at that temperature for 18 minutes during which a blue spectral sensitizing dye, anhydro-5-chloro-3,3'-di(3-sulfopropyl) naphtho[1,2-d]thiazolothiacyanine hydroxide triethylammonium salt (220 mg/Ag mol) was added, followed by stirring for 17 minutes. A solution of 1-(3-acetamidophenyl)-5-mercaptotetrazole (68 mg/Ag mol) was then added, and the emulsions stirred for another 10 minutes. Then a solution of potassium bromide (741 mg/Ag mol) was added. After another 15 minutes of stirring, the emulsions were allowed to cool to 40° C., at which time each emulsion's pH was adjusted to 4.9 with sodium hydroxide. The emulsions further contained a yellow dye-forming coupler alpha-(4-(4-benzylosy-phenyl-sulfonyl)phenoxy)-alpha (pivalyl)-2-chloro-5-(gamma-(2,4-di-5-amylphenoxy) butyramido)acetanilide (1.08 g/m²) in di-n-butylphthalate coupler solvent (0.27 g/m²), and gelatin (1.51 g/m²). The emulsions (0.34 g Ag/m²) were coated on a resin coated paper support and a 1.076 g/m² gel overcoat was applied as a protective layer along with the hardener bis(vinylsulfonyl) methyl ether in an amount of 1.8% of the total gelatin weight.

The coatings were exposed and processed as in Example 1. Speed and fog data were determined as in Example 1.

Amounts are shown in Table II in μmol/Ag mol. Data in Table II demonstrate that Speed and fog advantages provided by the present invention are also exhibited in cubic silver chloride emulsions.

TABLE II

| Sample | Compound | Amount | Speed | Fog |
|---|---|---|---|---|
| 25 (control) | none | 0 | * | 0.053 |
| 26 (invention) | A | 9.13 | 142 | 0.063 |
| 27 (invention) | A | 45.65 | 158 | 0.060 |
| 28 (comparison) | C-3 | 9.13 | 10 | 0.093 |
| 29 (comparison) | C-3 | 114.13 | 25 | 0.127 |

*Speed was too low as to be read

The invention has been described in detail with particular reference to the preferred embodiments thereof, but it will be understood that variations and modifications can be effected within the scope of the invention.

What is claimed is:

1. A photographic element comprising a support having situated thereon a silver halide emulsion layer, said emulsion layer comprising a compound of the formula:

$$Z-SO_2S-Au(I)-L \tag{I}$$

wherein

Z represents an alkyl, aryl, or heterocyclic group; and

L represents a thioether, selenoether or telluroether containing ligand.

2. A photographic element according to claim 1 wherein L has a molecular weight of from about 60 to about 2000.

3. A photographic element according to claim 2 wherein L has a molecular weight of from about 100 to about 500.

4. A photographic element according to claim 1 wherein L is of the formula:

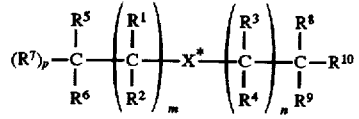

wherein

X is a sulfur or selenium atom;

* denotes the point of attachment of L to Au(I);

$R^1$ to $R^4$ are independently hydrogen or an alkyl, aryl or heteroaryl group;

$R^5$ and $R^6$ are bonded together to form an aryl or heteroaryl ring, or are independently hydrogen, carboxy, sulfo, amino, or an alkyl, aryl or heteroaryl group;

$R^7$, $R^8$, $R^9$ and $R^{10}$ are independently hydrogen, carboxy, sulfo, amino or an alkyl, aryl or heteroaryl group;

n and m are independently 0 to 20; and p is 0 or 1, with the proviso that if $R^5$ and $R^6$ are bonded together to form an aryl or heteroaryl ring, p is 0 and if $R^5$ and $R^6$ are not so bonded, p is 1.

5. A photographic element according to claim 4 wherein L is of the formula

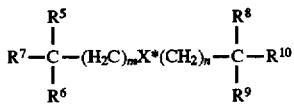

wherein

X is a sulfur atom;

* denotes the point of attachment of L to Au(I);

$R^5$ and $R^8$ are independently hydrogen or an alkyl group having from 1 to 10 carbon atoms or an aryl group having from 5 to 10 carbon atoms;

$R^6$, $R^7$, $R^9$ and $R^{10}$ are independently hydrogen, carboxy, amino or an alkyl group having from 1 to 6 carbon atoms; and n and m are independently 0 to 10.

6. A photographic element according to claim 4 wherein the emulsion layer is comprised of predominantly silver chloride.

7. A photographic element according to claim 6 wherein the compound is selected from the group consisting of:

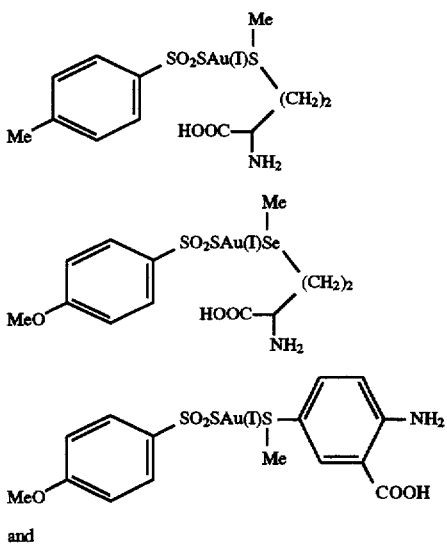

and

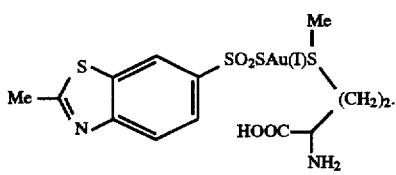

8. A photographic element comprising a support having situated thereon a silver halide emulsion layer, said emulsion layer having been chemically sensitized in the presence of a compound of the formula:

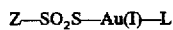   (I)

wherein

Z represents an alkyl, aryl, or heterocyclic group; and

L represents a thioether, selenoether or telluroether ligand.

9. A photographic element according to claim 8 wherein L has a molecular weight of from about 60 to about 2000.

10. A photographic element according to claim 9 wherein L has a molecular weight of from about 100 to about 500.

11. A photographic element according to claim 10 wherein L is of the formula:

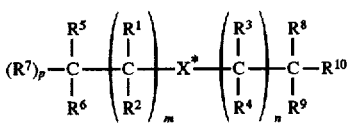

wherein

X is a sulfur or selenium atom;

* denotes the point of attachment of L to Au(I);

$R^1$ to $R^4$ are independently hydrogen or an alkyl, aryl or heteroaryl group;

$R^5$ and $R^6$ are bonded together to form an aryl or heteroaryl ring, or are independently hydrogen, carboxy, sulfo, amino, or an alkyl, aryl or heteroaryl group;

$R^7$, $R^8$, $R^9$ and $R^{10}$ are independently hydrogen, carboxy, sulfo, amino or an alkyl, aryl or heteroaryl group;

n and m are independently 0 to 20; and p is 0 or 1, with the proviso that if $R^5$ and $R^6$ are bonded together to form an aryl or heteroaryl ring, p is 0; and if $R^5$ and $R^6$ are not so bonded, p is 1.

12. A photographic element according to claim 11 wherein L is of the formula

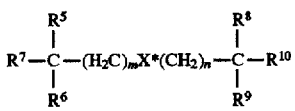

wherein

X is a sulfur atom;

* denotes the point of attachment of L to Au(I);

$R^5$ and $R^8$ are independently hydrogen or an alkyl group having from 1 to 10 carbon atoms or an aryl group having from 5 to 10 carbon atoms;

$R^6$, $R^7$, $R^9$ and $R^{10}$ are independently hydrogen, carboxy, amino or an alkyl group having from 1 to 6 carbon atoms; and n and m are independently 0 to 10.

13. A photographic element according to claim 11 wherein the emulsion layer is comprised of predominantly silver chloride.

14. A photographic element according to claim 13 wherein the compound is selected from the group consisting of:

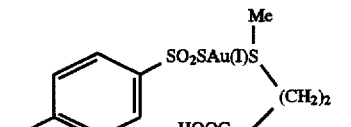

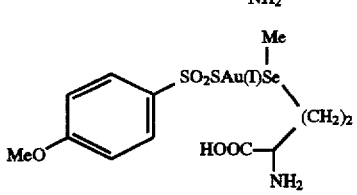

-continued

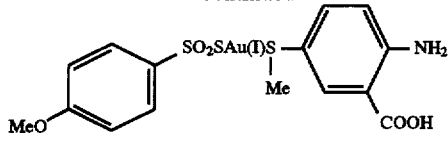

and

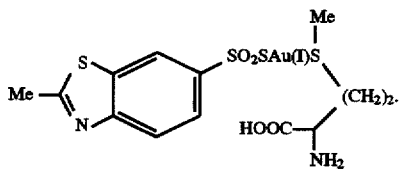

15. A method of forming a silver halide emulsion comprising precipitating silver halide grains in an aqueous colloidal medium, washing the grains, and sensitizing the grains by adding dyes, chemical sensitizers, and heating, and adding to the emulsion, prior to or during heating, a compound of the formula:

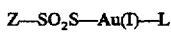     (I)

wherein

Z represents an alkyl, aryl, or heterocyclic group; and

L represents a thioether, selenoether or telluroether ligand.

16. A method according to claim 15 wherein the L is of the formula

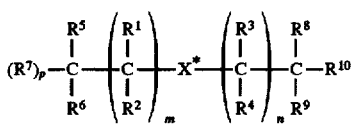

wherein

X is a sulfur or selenium atom;

* denotes the point of attachment of L to Au(I);

$R^1$ to $R^4$ are independently hydrogen or an alkyl, aryl or heteroaryl group;

$R^5$ and $R^6$ are bonded together to form an aryl or heteroaryl ring, or are independently hydrogen, carboxy, sulfo, amino, or an alkyl, aryl or heteroaryl group;

$R^7$, $R^8$, $R^9$ and $R^{10}$ are independently hydrogen, carboxy, sulfo, amino or an alkyl, aryl or heteroaryl group;

n and m are independently 0 to 20; and p is 0 or 1, with the proviso that if $R^5$ and $R^6$ are bonded together to form an aryl or heteroaryl ring, p is 0; and if $R^5$ and $R^6$ are not so bonded, p is 1.

17. A method according to claim 16 wherein the compound is selected from the group consisting of:

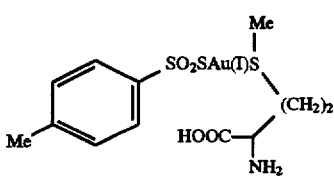

-continued

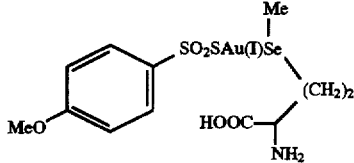

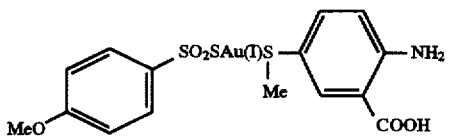

and

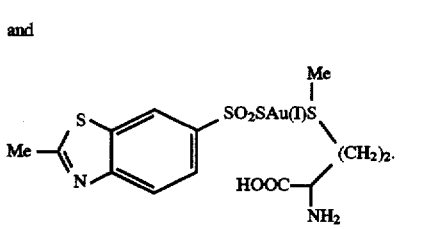

18. A photographic silver halide emulsion prepared by precipitating silver halide grains in a first aqueous colloidal medium, washing the grains, sensitizing the grains by adding dyes, chemical sensitizers and heating, and adding to the emulsion, prior to heating, a dispersion prepared by combining a thiosulfonate compound with potassium tetrachloraurate and a thioether, selenoether, or telluroether compound in a second aqueous colloidal medium.

19. A compound of the formula

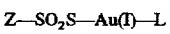     (I)

wherein

Z represents an alkyl, aryl, or heterocyclic group; and

L represents a thioether, selenoether or telluroether ligand.

20. A compound according to claim 19 wherein L is of the formula

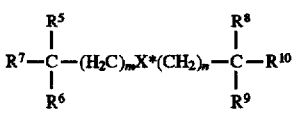

wherein

X is a sulfur atom;

* denotes the point of attachment of L to Au(I);

$R^5$ and $R^8$ are independently hydrogen or an alkyl group having from 1 to 10 carbon atoms or an aryl group having from 5 to 10 carbon atoms;

$R^{6,}$ $R^7$, $R^9$ and $R^{10}$ are independently hydrogen, carboxy, amino or an alkyl group having from 1 to 6 carbon atoms; and n and m are independently 0 to 10.

* * * * *